United States Patent [19]

Hirata et al.

[11] Patent Number: 4,650,869
[45] Date of Patent: Mar. 17, 1987

[54] DX-52-1 COMPOUNDS AND PROCESS FOR PREPARING THE SAME

[75] Inventors: Tadashi Hirata, Yokohama; Shigeru Kobayashi, Sagamihara; Keiichi Takahashi, Machida; Makoto Morimoto, Shizuoka; Yuko Arai, Susono, all of Japan

[73] Assignee: Kyowa Hakko Kogyo Co., Ltd., Tokyo, Japan

[21] Appl. No.: 606,902

[22] Filed: May 4, 1984

[30] Foreign Application Priority Data

May 13, 1983 [JP] Japan ................................. 58-83775

[51] Int. Cl.$^4$ ................. C07D 487/18; C07D 498/22; A61K 31/495
[52] U.S. Cl. .................................... 544/343; 544/342
[58] Field of Search ......................................... 544/343

[56] References Cited

PUBLICATIONS

Danishefsky, Chem. Abs. 102, 95887f (1984).
Kyowa Chemical Abstracts, vol. 98, 1983, p. 416, No. 86722z.

Primary Examiner—Mark L. Berch
Attorney, Agent, or Firm—Fitzpatrick, Cella, Harper & Scinto

[57] ABSTRACT

A compound represented by the formula:

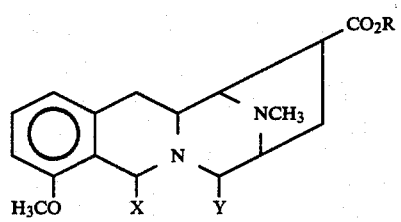

wherein r is a hydrogen atom or a lower alkyl group, X is a hydroxymethyl group and Y is a cyano group, and when R is a lower alkyl group, X and Y may combine to form —$CH_2$—O—, and salts thereof, process for preparing the same, and an anti-tumor composition containing the same, which is improved in stability in comparison with a starting compound DC-52.

3 Claims, No Drawings

DX-52-1 COMPOUNDS AND PROCESS FOR PREPARING THE SAME

BACKGROUND OF THE INVENTION

This invention relates to a compound represented by the formula (I):

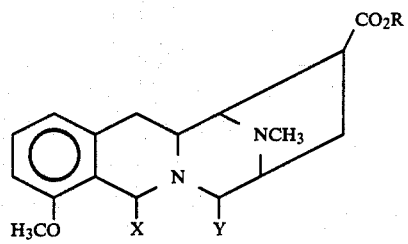

(wherein R is a hydrogen atom or a lower alkyl group, X is a hydroxymethyl group and X is a cyano group and when R is a lower alkyl group, X and Y may combine to form —$CH_2$—O—) [hereinafter referred to as compound (I)] and salts thereof, and to a process for preparing the same.

Among compounds (I), a compound wherein X is a hydroxymethyl group, Y is a cyano group and R is a hydrogen atom (hereinafter referred to as DX-52-1) and its alkyl esters are novel substances prepared by reacting DC-52 or its lower alkyl ester represented by the general formula (II):

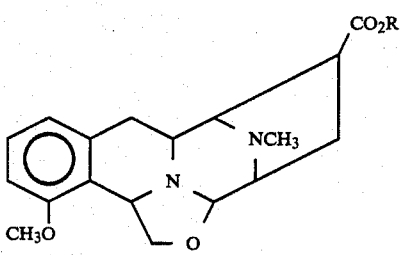

(where R is a hydrogen atom or a lower alkyl group) with cyanide ions.

DC-52 [R=hydrogen atom in formula (II)] is an antibiotic disclosed in Japanese Published Unexamined Patent Application No. 17089/1982, which is a useful substance having an antibacterial activity against various bacteria, and also anti-tumor activity against sarcoma 180 ascites tumor, lymphocytic leukemia P-388, etc., but it has a problem in stability.

DX-52-1, its alkyl esters and salts thereof have an antibacterial activity against various bacteria and also an anti-tumor activity and have a significantly improved stability over DC-52.

DETAILED DESCRIPTION OF THE INVENTION

In formula (I), the lower alkyl group represented by R is exemplified by straight or branched alkyls of $C_1$–$C_5$ such as methyl, ethyl, n-propyl, i-propyl, n-butyl, i-butyl and n-pentyl.

DX-52-1 or its alkyl esters can be prepared in the following manner:

DC-52 or its lower alkyl ester is reacted with a cyanide ion-liberating compound such as sodium cyanide, potassium cyanide, copper cyanide, mercury cyanide, etc. in water alcohols such as methanol, ethanol and n-butanol, or a solvent mixture of water and an alcohol or an organic solvent such as acetone, acetonitrile, dimethylsulfoxide, dimethylacetamide, hexamethylphosphoryltriamide, etc. at a freezing point of the solvent to 50° C., and DX-52-1 or its lower alkyl ester formed in the solution is isolated according to the ordinary separating procedure. A separating and purifying procedure comprises, for example, passing the solution as such or after concentration through a non-ionic porous resin (for example, Diaion HP-20SS, a product of Mitsubishi Kasei Kogyo Co. Ltd.) to adsorb DX-52-1 or its lower alkyl ester, and then desorbing DX-52-1 or its lower alkyl ester with water, acetone, methanol, ethanol, acetonitrile, etc, or a mixture thereof, whereby DX-52-1 or its lower alkyl ester can be separated and purified.

Besides the non-ionic porous resin, ion exchange resins, Sephadex, or adsorbing-desorbing carriers such as silica gel can be used. When the reaction solution is passed through the non-ionic carrier after the reaction with a metal cyanide, DX-52-1 may be recovered as a corresponding metal salt of carboxylic acid.

Compounds (I) wherein R is a lower alkyl group and X and Y combine to form —$CH_2$—O—, that is, DC-52 lower alkyl esters are also novel compounds having an anti-bacterial activity and an anti-tumor activity, and can be prepared by reacting DC-52 with an ethereal solution of corresponding diazo-lower alkane such as diazomethane and diazoethane in a lower alcohol such as methanol and ethanol or its mixture with water.

Lower alkyl esters of DX-52-1 can also be prepared by reaction of DX-52-1 with a corresponding diazoalkane in the same manner as above.

DX-52-1 may exist in an undessociated form or as an intramolecular salt, as shown by the following formula, depending upon the pH of a solvent.

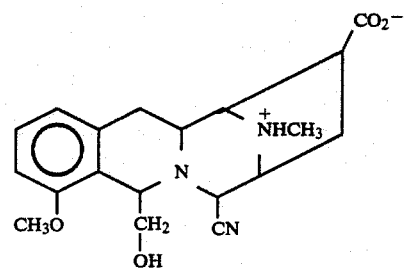

DC-52 and its alkyl ester may also exist in a hydrated form in an aqueous solution as shown by the following formula.

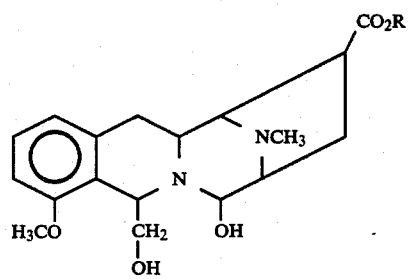

Salts of compound (I) are exemplified by metallic salts of carboxylic acid such as sodium salt, potassium salt, calcium salt and magnesium salt, salts of carboxylic acid with organic bases such as triethylamine, lysine, ornithine and arginine, salts of tertiary amine with mineral acids such as hydrochloride and sulfate, and salts of tertiary amine with organic acids such as acetate, fumarate, maleate, succinate, lactate and malate.

According to a further feature of the present invention, there is provided an anti-tumor composition, comprising as active ingredient a compound (I) or a salt thereof in association with at least one pharmaceutically acceptable carrier or excipient. The carrier or excipient may take various forms depending upon the desired formulation. Thus, for example, compound (I) or its salt may be dissolved in a physiological saline solution, or a solution of glucose, lactose or mannitol to formulate an anti-tumor composition suitable for injection.

Alternatively, it is possible to freeze-dry a compound (I) or its salt according to a conventional method, to which sodium chloride is added to prepare a powdery injection agent. The composition may, if desired, comprise conventional additives or excipients such as pharmaceutically acceptable salts which are well known in the pharmaceutical art. The composition can be administered to a human being in an amount of 0.1 to 2 mg/kg/day as a compound (I) though the dosage may vary depending upon age, condition, etc. of the patient. The administration may be effected, for example, by intravenous injection made continuously once a day, or intermittently once a week or once three weeks.

If desired, oral administration is possible. Dosage forms suitable for oral administration may, for example, include tablets, powders, granules and ampoules which contain as additional components appropriate excipients, etc. well known in the pharmaceutical art. If desired, intraarterial administration, intraperitoneal administration, intrapleural administration, etc. is practicable.

Acute toxicities ($LD_{50}$) of DX-52-1 and DC-52 methyl ester by intraperitoneal administration in mice are 24.5 mg/kg and 71.3 mg/kg, respectively.

The present invention will be described below, referring to examples, test examples and reference examples.

EXAMPLE 1

Preparation of DX-52-1

At first, 2.0 g of sodium cyanide is dissolved in 30 ml of 0.1M phosphate buffer (pH 7.4) and 1 g of crude DC-52-(containing 0.6 g of DC-52) is added thereto. The mixture is stirred at room temperature for 1.5 hours. The reaction mixture is passed through a column containing 200 ml of Diaion HP-20SS (made by Mitsubishi Chemical Industries Co., Ltd.), and the column is developed and eluted with 1 l of water (fraction Nos. 1–160; 6 ml each), and then with 1% acetone-99% water (by volume; fraction Nos. 161–224, 6 ml each). Fraction Nos. 125–165 and fraction Nos. 166–199 are joined together separately, and concentrated under reduced pressure, followed by freeze-drying to obtain 161 mg of fraction A and 179 mg of fraction B.

Then, 161 mg of fraction A is dissolved in 0.5 ml of an aqueous sodium bicarbonate solution, and the solution is passed through a column containing 9 ml of Diaion HP-20SS. The column is developed and eluted with water, and fraction Nos. 18–43, 1 ml each, are joined together, concentrated under reduced pressure, and freeze-dried to obtain 103 mg of light yellow sodium salt of DX-52-1.

Separately, 179 mg of fraction B is likewise subjected to column chromatography of Diaion HP-20SS, and the column is developed and eluted with water. Fraction Nos. 13–16, 1 ml each, are joined together, concentrated under reduced pressure and freeze-dried to obtain 83 mg of light yellow sodium salt of DX-52-1.

Physical properties of these products are given below:

$[\alpha]_D^{20} = 22°$ (c=0.19, MeOH).

Mass analysis: M+ 501 for DX-52-1.2TMS.

IR spectrum $\nu_{max}^{KBr}$ (cm$^{-1}$): 3410, 2950, 1588, 1563, 1473, 1403, 1395, 1262, 1100, 1075.

PMR spectrum:

(1) PD8.8 in $D_2O$

δ(ppm): 7.4–7.1(1H, m), 7.0–6.7(2H, m), 4.23(1H, d, J=2.9 Hz), 4.14(1H, t, J=3.7 Hz, 3.7 Hz), 3.82(3H, s), 3.7–3.4(4H, m), 3.2–2.95(1H, m), 2.9–2.3(4H, m), 2.22(3H, s), 2.03(1H, dd, J=10.0 Hz, 13.4 Hz).

(2) PD6.1 in $D_2O$-DCl

δ(ppm): 7.4–7.1(1H, m), 7.0–6.7(2H, m), 4.49(1H, d, J=2.4 Hz), 4.3–4.1(1H, m), 4.05–3.85(2H, m), 3.82(3H, s), 3.68(1H, d, J=3.2 Hz), 3.64(1H, d, J=5.1 Hz), 3.4–3.15(1H, m), 3.1–2.55(4H, m), 2.54(3H, s), 2.25(1H, dd, J=10.5 Hz, 13.9 Hz).

(3) PD3.5 in $D_2O$-DCl

δ(ppm): 7.4'7.1(1H, m), 7.0–6.8(2H, m), 4.75(1H, d, J=2.4 Hz), 4.5–4.1(3H, m), 3.83(3H, s), 3.75–3.4(3H, m), 3.35–3.0(1H, m), 2.87(3H, s), 2.9–2.3(4H, m).

CMR (value on TMS Standard in $D_2O$, using 67.4 ppm for dioxane) δ(ppm): 183.7, 156.4, 138.1, 129.0, 122.4, 121.4, 119.4, 110.1, 70.8, 65.5, 65.2, 58.7, 58.4, 58.3, 56.3, 45.1, 41.8, 33.0, 30.0.

Thin layer chromatography [silica gel (kieselgel 60$^F$254 Art 5715, a product of E. Merck Co.] shows the following $R_f$ values:

| Developing solvent | $R_f$ value |
|---|---|
| Methanol | 0.69 |
| Ethanol:Water = 10:1 (by volume) | 0.53 |
| n-Butanol:Ethanol:Water = 4:1:1 (by volume) | 0.39 |

Spots of DX-52-1 after the development can be detected by bioassay using *Bacillus subtilis*, spray of hot sulfuric acid or iodine, nitroprusside reaction, ninhydrin reaction, Ehrlich's reagent, Dragendroff reaction, or ultraviolet absorption.

Furthermore, 9.46 g of crude DX-52-1 sodium salt is dissolved in 10 ml of water and 6N hydrochloric acid is added thereto to make a solution of pH 2. Then, the solution is subjected to column chromatography with 600 ml of Diaion HP-20 (adsorption resin made by Mitsubishi Chemical Industries Co., Ltd., Japan). The column is washed with 4 l of water, 2 l of 2% aqueous methanol, 2 l of 5% aqueous methanol, 1 l of 10% aqueous methanol and 3 l of 5% aqueous acetone and then eluted with 20% aqueous acetone. The eluates are combined and concentrated under reduced pressure. The residue is subjected to column chromatography of 220 ml of Wako-gel C-200 (silica gel made by Wako Junyaku Co., Ltd., Japan). That is, the residue is charged with methanol and washed with 500 ml of chloroform. The fractions eluted with chloroform:methanol=10:1 are combined and concentrated under reduced pressure. The residue is crystallized from methanol and ethyl ether to obtain 2.08 g of DX-52-1 hydrochloride.

IR spectrum $\nu_{max}^{KBr}$ (cm$^{-1}$): 3350, 1738, 1592, 1473, 1267, 1139, 1072, 1057.

EXAMPLE 2

Preparation of DX-52-1 methyl ester.

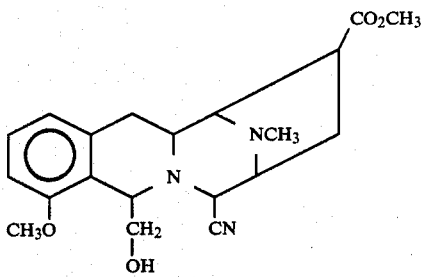

At first, 10 mg of methyl ester of DC-52 obtained in the same manner as in Example 4 is dissolved in 0.1 ml of water, 0.1 ml of acetonitrile and 0.1 ml of 0.1M phosphate buffer (pH 7.4). Then, 12 mg of sodium cyanide is added thereto, and the mixture is stirred at room temperature for 6 hours. The reaction mixture is subjected to silica gel thin layer chromatography (Kieselgel Art 5715; developing solvent: n-butanol:ethanol:water=4:1:1), and spots of $R_f$ value about 0.78 are scraped off and extracted with methanol. The extract is concentrated under reduced pressure, and freeze-dried to obtain 2.8 mg of the desired compound having the following physical properties;

Melting point: 178.5°–180.5° C.

Mass analysis: M+ 371.

IR spectrum $\nu_{max}^{CHCl_3}$ (cm$^{-1}$): 3010, 2960, 1733, 1722, 1595, 1480, 1460, 1440, 1270, 1210.

PMR spectrum (CDCl$_3$) δ(ppm): 7.25–6.95(1H, m), 6.8–6.5(2H, m), 4.35–4.1(1H, m), 4.05(1H, d, J=2.7 Hz), 3.79(3H, s), 3.73(3H, s), 3.7–3.3(4H, m), 3.25–2.9(2H, m), 2.8–2.4(3H, m), 2.33(3H, s), 2.00(1H, dd, J=9.5 Hz, 13.2 Hz).

CMR spectrum (CDCl$_3$) δ(ppm): 175.91, 155.83, 136.19, 127.81, 122.05, 120.44, 117.82, 108.59, 70.45, 65.79, 64.70, 58.03, 57.84, 57.60, 55.32, 52.24, 42.77, 41.91, 32.96, 28.91.

EXAMPLE 3

Preparation of DX-52-1 methyl ester (alternative procedure)

At first, 42 mg of DX-52-1 is dissolved in 1 ml of methanol, and an ethereal solution of diazomethane is added to the solution until no N$_2$ gas is generated. The mixture is stirred at room temperature overnight, and then a few drops of acetic acid is added thereto. Then, the mixture is concentrated under reduced pressure, and the residue is subjected to silica gel chromatography (Wako gel C-200 8 ml, developing solution: chloroform:acetone=20:1) to obtain 2 ml each of fractions. The third and fourth fractions are joined together, concentrated under reduced pressure, and freeze-dried to obtain 41.4 mg of the desired compound as a light yellow oily product (74.6%).

EXAMPLE 4

Preparation of DC-52 methyl ester hydrochloride

At first, 200 mg of DC-52 is dissolved in 10 ml of methanol, and an ethereal solution of diazomethane is added in excess to the solution. The mixture is stirred at room temperature for one hour, and then the solvent is removed therefrom by distillation. The residue is subjected to silica gel (100 ml) chromatography. From fractions of chloroform-methanol (99.5:0.5 V/V) DC-52 methyl ester is obtained as a single substance. Monitoring of the substance is carried out by iodine coloring in silica gel TLC (CHCl$_3$:MeOH=95:5 V/V). The thus obtained DC-52 methyl ester is dissolved in ether or a small amount of methanol, and a dry ethereal solution saturated with hydrogen chloride gas is added to the solution, whereby DC-52 methyl ester hydrochloride is formed as colorless powders. The precipitate is recovered by filtration with suction, and thoroughly washed with ether to obtain 180 mg of DC-52 methyl ester hydrochloride as a single product.

Physical properties of the product are as follows:

Melting point: coloring starts at about 140° C. and decomposition at about 180° C., with no specific melting point.

Specific rotation: $[\alpha]_D^{20}$=−33.6° (c=0.5, H$_2$O).

Ultraviolet absorption spectrum (in H$_2$O): 271, 277 nm.

IR spectrum $\nu_{max}^{KBr}$ (cm$^{-1}$): 3380, 1725, 1590, 1470, 1265.

$^{13}$C-NMR spectrum (in D$_2$O, dioxane=67.4 ppm standard) δ(ppm): 175.8(s), 156.5(s), 136.8(s), 129.0(d), 123.3(s), 121.2(d), 110.4(d), 82.1(d), 70.8(d), 69.6(d), 66.0(t), 56.4(q), 54.5(d), 54.2(q), 53.9(d), 40.5(q), 39.6(d), 31.8(t), 26.9(t).

PMR spectrum (D$_2$O) δ(ppm): 2.5–2.8(4H, m), 2.81(3H, s), 3.7–3.3(4H, m), 3.83(6H, s), 3.9–4.0(1H, m), 4.32(1H, br.s), 4.48(1H, t, J=3.5 Hz), 4.96(1H, d, J=3.2 Hz), 6.80–7.36(3H, m).

Solubility: readily soluble in water, methanol and ethanol; soluble in chloroform and acetone; insoluble in ethyl ester and n-hexane.

TEST EXAMPLE 1

Antibacterial activities of DX-52-1 against some bacteria (agar dilution method, pH 7.0) are given below:

| Test bacteria | Minimum inhibitory concentration (μg/ml) |
|---|---|
| Staphylococcus aureus ATCC 6538P | >100 |
| Bacillus subtilis #10707 | 16.7 |
| Klebsiella pneumoniae ATCC 10031 | >100 |
| Proteus vulgaris ATCC 6897 | 16.7 |
| Escherichia coli ATCC 26 | >100 |

TEST EXAMPLE 2

Antibacterial activites of DC-52 methyl ester hydrochloride against various bacteria (agar dilution method, pH 7.0) are given below.

| Test bacteria | Minimum inhibitory concentration (μg/ml) |
|---|---|
| Staphylococcus aureus ATCC 6538P | 12.5 |
| Bacillus subtilis #10707 | 6.5 |
| Klebsiella pneumoniae ATCC 10031 | 2.5 |
| Escherichia coli ATCC 26 | >100 |
| Shigella sonnei ATCC 9290 | >100 |
| Salmonella typhosa ATCC 9992 | 50 |

TEST EXAMPLE 3

Effect on Lymphocytic Leukemia P-388 Tumor

Five male CDF$_1$ mice having a weight of about 22 g were used for each group as test animals; and 1×10$^6$ cells of Lymphocytic leukemia P-388 tumor were implanted intraperitoneally in the test animals. Twentyfour hours after implantation, 0.2 ml of physiological saline solution containing each test compound in various concentrations was administered intraperitoneally. T/C% after implantation and optimum dosage are given in Table 1.

TABLE 1

| Test compound | Method of administration | Optimum dosage (mg/kg) | T/C*3 (%) |
|---|---|---|---|
| DX-52-1 | x1*1 | 18.75 | 129 |
|  | x7*2 | 9.38 | 189 |
| DC-52 methyl ester | x1*1 | 50.00 | 120 |
|  | x7*2 | 6.25 | 105 |

*1 administered once 24 hours after the implantation
*2 administered once a day for continuous 7 days starting from 24 hours after the implantation.

*3 T/C(%) = $\dfrac{\text{The mean survival time (day) of the groups administered with test compound}}{\text{The mean survival time (day) of the control which is administered intraperitoneally with 0.2 ml of physiological saline solution.}} \times 100$

TEST EXAMPLE 4

Stability of DX-52-1

DX-52-1 and DC-52 were dissolved respectively in acetonitrile:phosphate buffer (pH 7.0) (1:4) and incubated at 25° C. for 6 hours. Amount of each compound remaining was determined with area intensity at 271 nm by high performance liquid chromatography.

|  | Remaining ratio (%) |
|---|---|
| DX-52-1 | 93 |
| DC-52 | <25 |

REFERENCE EXAMPLE 1

An injection is prepared by adding distilled water to 5 g of DX-52-1 and 50 g of glucose to make 1 l of a solution. The solution is filtered under pressure (0.5 Kg/cm$^2$) using a membrane filter having a 0.22$\mu$ pore size (Millipore Company, FGLD 14200) and N$_2$ gas. Portions of the filtrate are then poured into 20 ml-white ampoules and sealed under standard practices.

What is claimed is:

1. A compound represented by the formula:

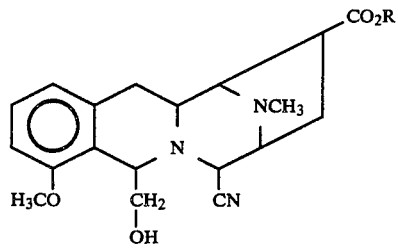

wherein R is a hydrogen atom or a lower alkyl group, and salts thereof.

2. A compound according to claim 1, wherein said salt is either a metallic or an organic gase salt of the compound's carboxylic acid; or a mineral or organic acid salt of the compound's tertiary amine.

3. A compound according to claim 1, wherein said salt is a sodium salt, potassium salt, calcium salt, magnesium salt, salt with triethylamine, lysine, ornithine or arginine, chloride, sulfate, acetate, fumarate, maleate, succinate, lactate or malate.

* * * * *